(12) United States Patent
Yao et al.

(10) Patent No.: US 6,932,505 B2
(45) Date of Patent: Aug. 23, 2005

(54) DENTAL X-RAY CLAMPING DEVICE WITH A MULTI-ORIENTATION SUPPORT

(76) Inventors: Yin-Chao Yao, No. 40, Tsu Hu Road, Ta Hsi, Taoyuan Hsien (TW); Tai-Ching Lin, No. 40, Tsu Hu Road, Ta Hsi, Taoyuan Hsien (TW)

( * ) Notice: Subject to any disclaimer, the term of this patent is extended or adjusted under 35 U.S.C. 154(b) by 0 days.

(21) Appl. No.: 10/682,123

(22) Filed: Oct. 10, 2003

(65) Prior Publication Data

US 2005/0047550 A1 Mar. 3, 2005

(51) Int. Cl.7 .................................................. A61B 6/14
(52) U.S. Cl. ........................................ 378/170; 378/191
(58) Field of Search ........................... 378/191, 168–170

(56) References Cited

U.S. PATENT DOCUMENTS

| | | | |
|---|---|---|---|
| 4,866,750 A | * | 9/1989 | Chavarria et al. .......... 378/168 |
| 5,737,388 A | * | 4/1998 | Kossila ....................... 378/168 |
| 6,102,566 A | * | 8/2000 | Willis ........................ 378/170 |
| 6,592,256 B2 | * | 7/2003 | Da Rold et al. ............ 378/168 |

* cited by examiner

Primary Examiner—Craig E. Church
Assistant Examiner—Krystyna Suchecki
(74) Attorney, Agent, or Firm—Troxell Law Office, PLLC (57) ABSTRACT

This invention is mainly to provide a dental x-ray clamping device with a multi-orientation support made up with an attachable ring pivot and a supporting-frame pivot, which is designed for an all-purpose modulized raying clamp with simplified members in design, in which the ring pivot is provided with a pivoting ring, while the supporting-frame pivot is provided with a pivoting supporting bite frame, and only the supporting bite frame is pivoted to an opening side of a supporting orientation and combined with the ring pivot easily pivoting at a required angle of rotation so as to be located at an orientation so that the center of the ring aligns with that of the opening side of the supporting bite frame and further that the x-ray operation can be performed at the case of the teeth diagnosis or the endodontic treatment using each orientational support on the teeth.

9 Claims, 14 Drawing Sheets

Fig. 1

Prior Art

DENTAL X-RAY CLAMPING DEVICE WITH A MULTI-ORIENTATION SUPPORT

FIELD FOR THE INVENTION

This invention relates to a raying clamp with an x-ray assistant film support at the time of a dental diagnosis or an endodontic treatment and particularly to a dental x-ray clamping device with a multi-orientation support so as further to be applied to the support to each orientation towards teeth for the dental x-ray diagnosis or the endodontic treatment as a x-ray operation.

BACKGROUND OF THE INVENTION

Generally, diagnosing a patient's teeth, a dentist uses the x-ray operation to know the pathological changes of teeth for follow-up diagnoses.

Figure 1:
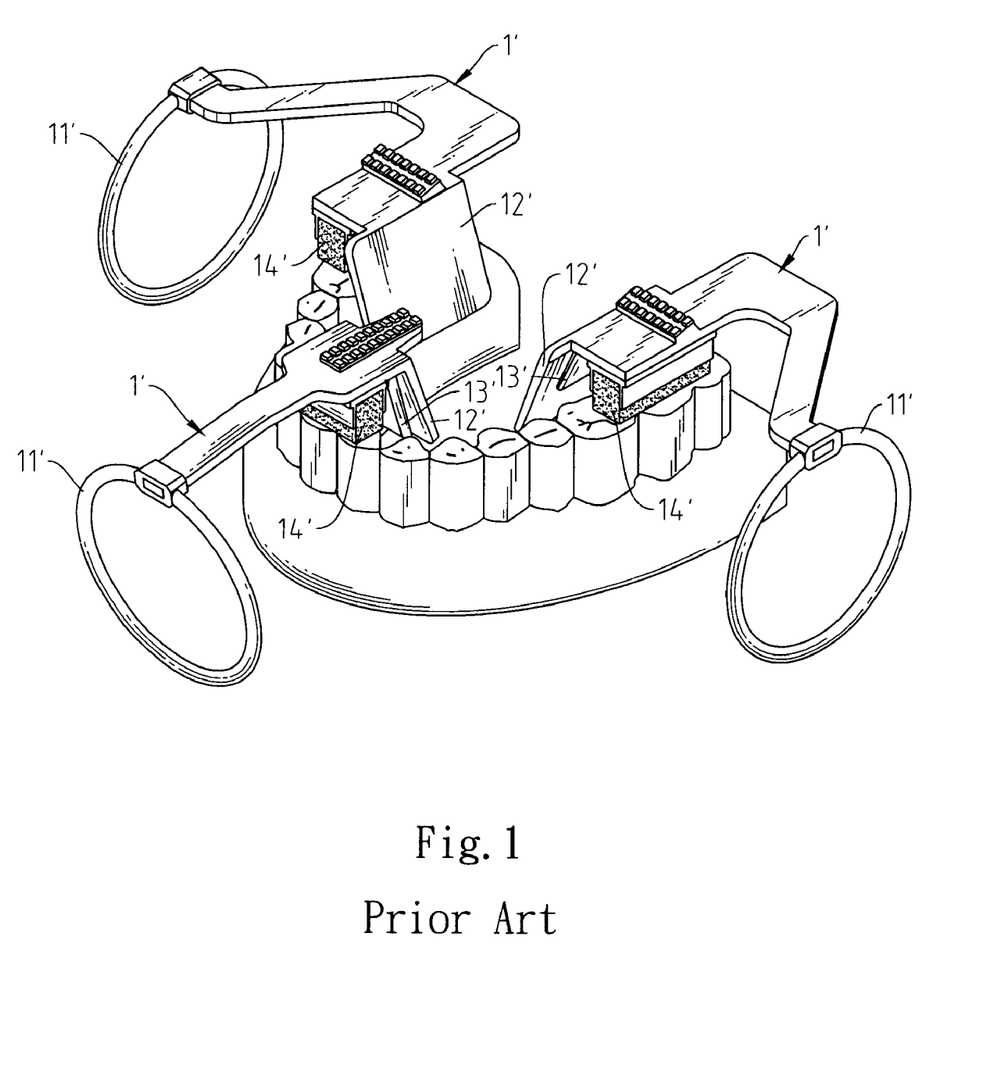
FIG. 1 shows three types of fixed raying clamp supported on the teeth for an x-ray operation according to an embodiment.

Further, in order to provide a solution to the x-ray operation relying on a manual pressing of the film for orientation, a clamping device is designed by this industry. As shown in FIG. 1, a conventional raying clamp currently used by the dentist is provided, in which a front end of a fixing frame 1' is fixed with a ring 11' to assist the x-ray to ray and focus and a back end stretching is provided with a supporting bite frame 12' fitted at one side with a flexible clip 13' clamped by the film; also, the fixing frame 1' at a section where teeth occlude with each other is also provided with a soft protective colloid 14' to reduce the pressure of the tooth when the teeth bite the raying device for the x-ray operation.

This conventional fixing raying device in a concrete application needs 3 sets of fixing raying clamp at a front side, a left side, and a right side of teeth to perform the x-ray operation (as shown in FIG. 1); the fixing frame 1' design of each set of the raying clamp varies from a different mounted position, and natural occlusion of teeth in a mouth is preferably kept for a required appearance. As shown in the figure, the fixing frame 1' of the support at the front of teeth is linearly designed, and the frame 1' of the support at the two sides of teeth is designed outward at different directions for appearance; relatively, when the support at the upper half portion of teeth is operated for x-ray, the three sets of fixed raying may reverse the support for the x-ray operation; that is to say, the raying clamp required for a right side of the lower half portion may directly reverse the support to a left side of the upper half portion of teeth for a common use, the raying clamp provided for the left side of the lower half portion may directly reverse the support to the right side of the upper half portion of teeth for a common use, and the raying clamp provided for a front side of the lower portion may directly reverse the support to the front side of the upper half side of teeth for a common use. For this reason, when the fixed raying clamp is operated for x-ray, the fixed raying clamp of three sets of different fixing frame 1' configured must be used for implementation of this operation, and it always takes much time and work that an orientation of the support is determined at the case of a raying operation; relatively, a multiple sets of raying clamp modules will cost much more, so economic benefits does disagree.

Further, when the dentist performs the endodontic treatment to the patient's teeth, he/she will put a reamer into the teeth for x-ray operation, thereby identifying an exact length of the treated tooth. However, the conventional designed fixed raying clamp is not suitable for the endodontic treatment because the reamer is put on the area where the teeth occlude, on which the fixed raying clamp is supported, so that the soft protective colloid 14' will hinder the reamer, thereby causing a not ideal application.

Figure 2:
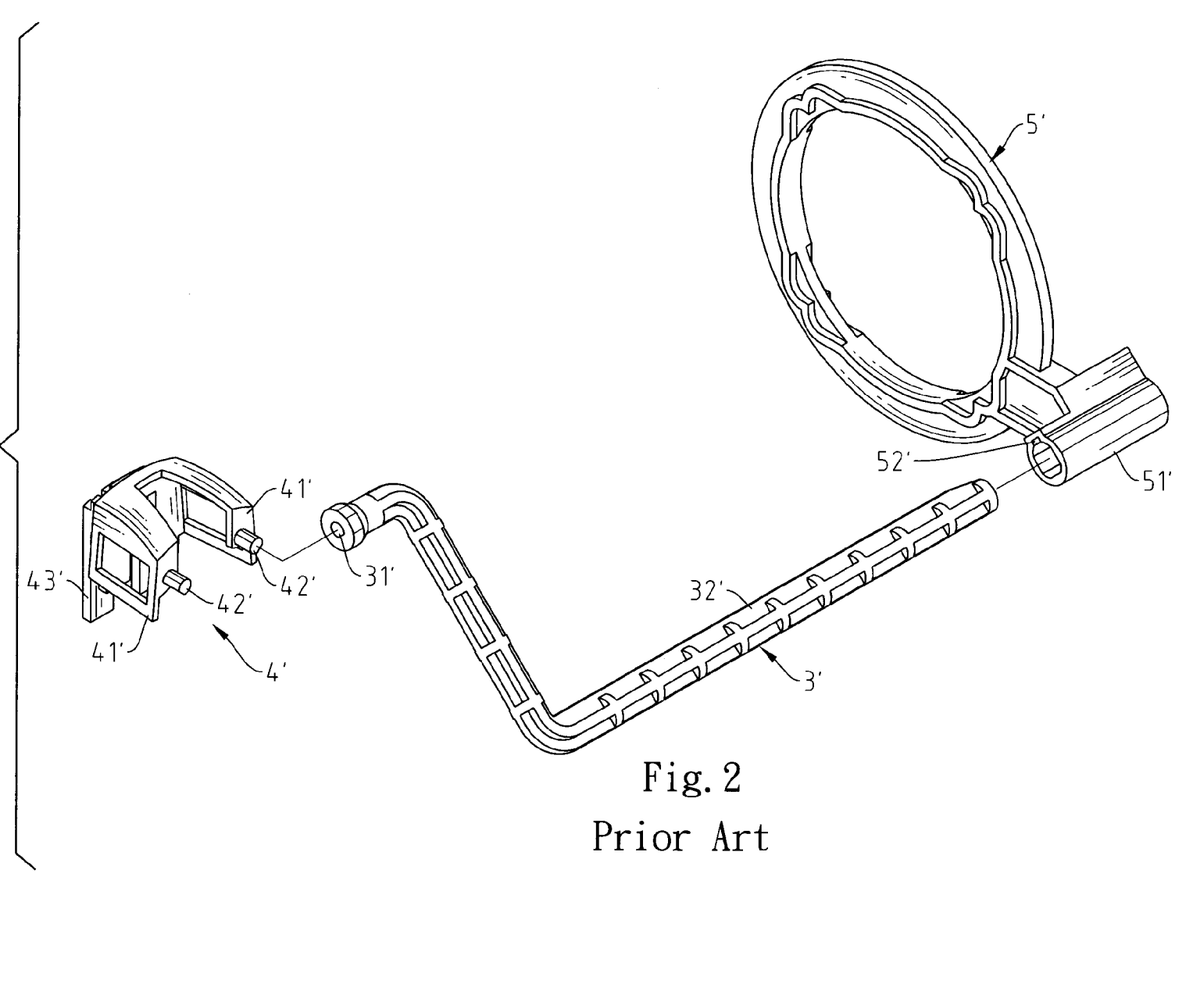
FIG. 2 shows a schematic view of exploded members of a conventional raying clamp attachable.

In order to allow the raying clamp to be used in teeth diagnosis and endodontic treatment, an attachable raying clamp, as shown in FIG. 2, is further provided in this industry, organized with a two-way attachable master shaft 3', a supporting bite frame 4', and a ring 5', in which one end of the major shaft 3' is provided with concaved directional wedge slot 31' for an insertion, the body of the major shaft 3' is formed with a protruding wedge strip 32', and two side frames of the two butt sides of the bite frame 4' are separately protruded with a directional protruding tenon 42' for insertion to correspondingly wedge the slot 31' of the major shaft 3' so that the major shaft 3' may be connected to a left or right side of the supporting bite frame 4' and further the bite frame 4' is provided with a clip 43' on a side of a shield for allocation, while a side of the ring 5' is protruded with a hollow shaft 51' to be put around the body of the major shaft 3', in which a rabbet 52' is provided in the hollow shaft 51' to wedge the wedge strip 32' of the major shaft 3' so that the ring may only at a direction be fixedly put around the body of the major shaft 3'.

Figure 3:
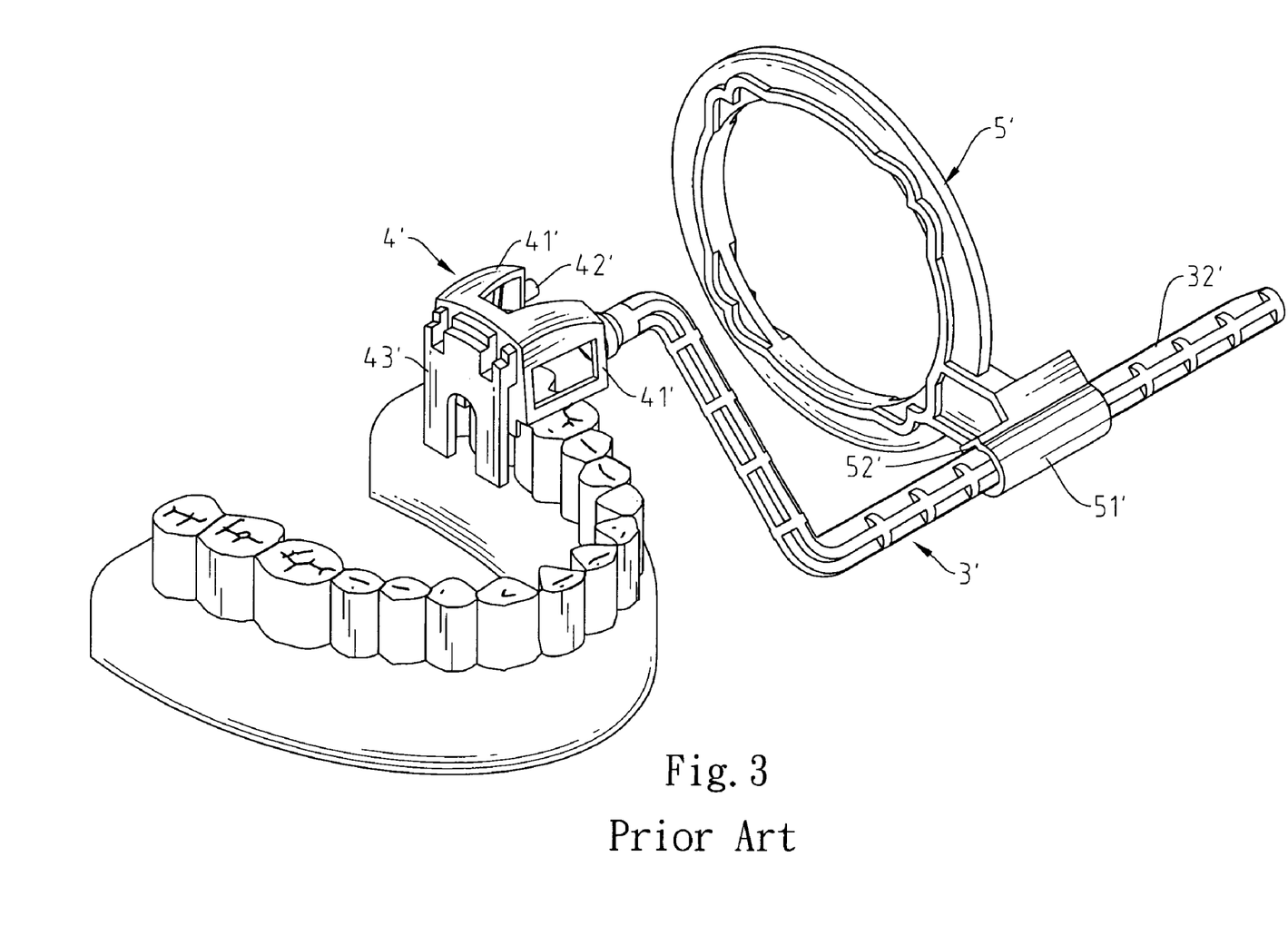
FIG. 3 shows a conventional attachable raying clamp supported at a left side of a lower half portion of the teeth for the x-ray operation according to the embodiment.
Figure 4:
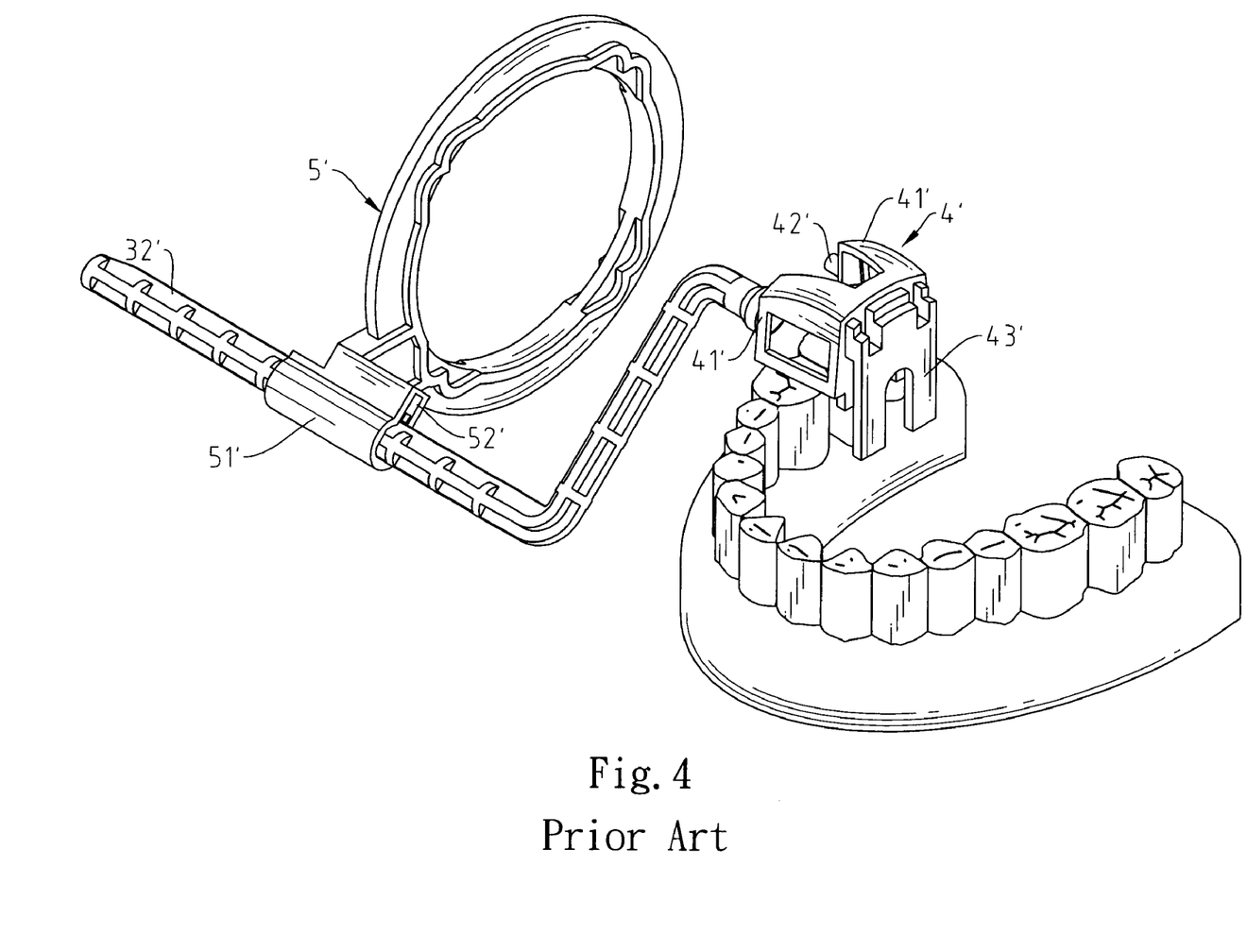
FIG. 4 shows a conventional attachable raying clamp supported at a right side of the lower half portion of the teeth for the x-ray operation according to the embodiment.
Figure 5:
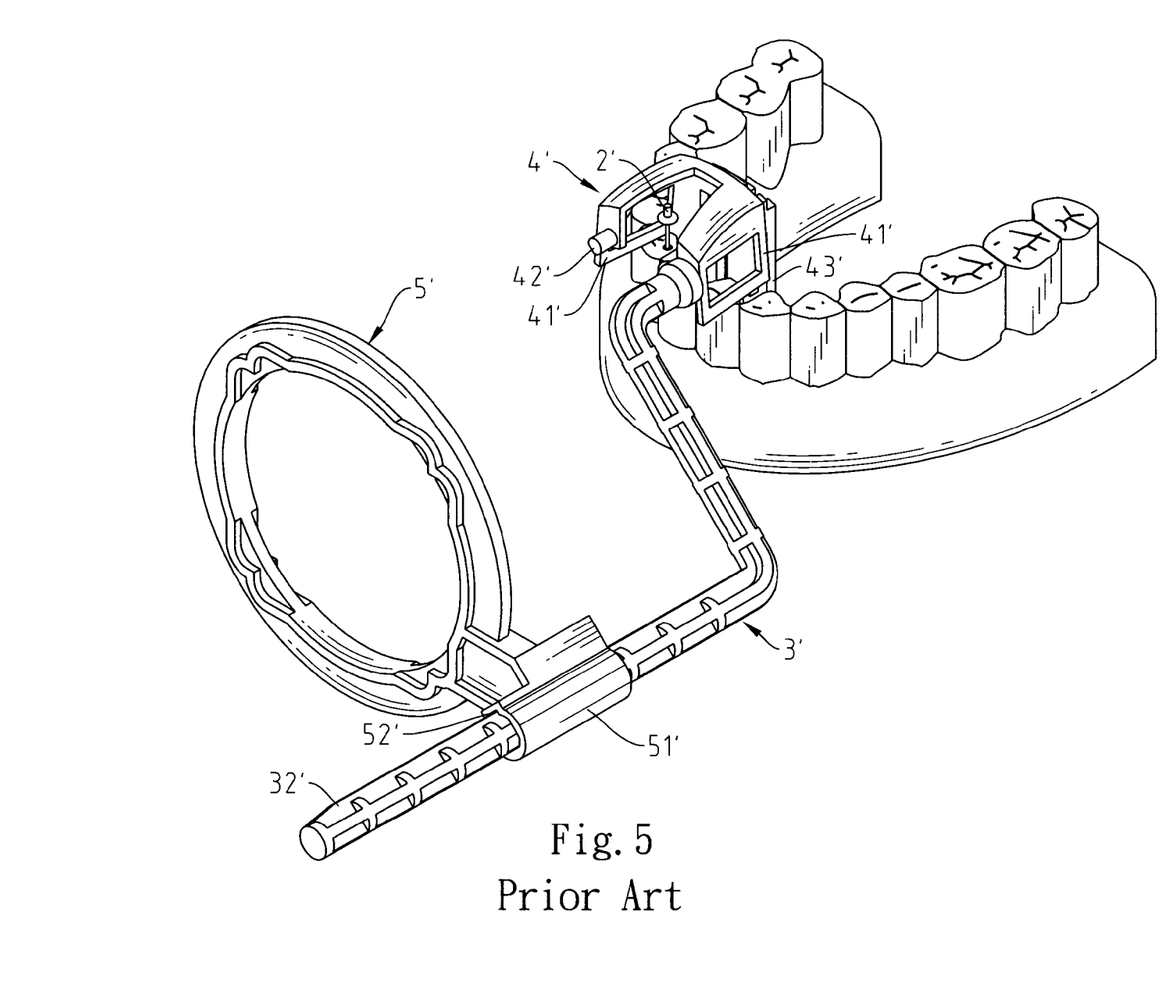
FIG. 5 shows the conventional attachable raying clamp supported at a front side of the lower half portion of the teeth according to the embodiment.

When the attachable raying clamp is concretely applied to the x-ray operation at the two sides of teeth, as shown in FIGS. 3 and 4, the major shaft 3' is used to connect with the supporting bite frame 4' and the ring 5' and the major shaft 3' is oriented to the supporting bite frame 4', namely the major shaft 3' being fixed to a left or right side of the supporting bite frame 4', and works with the shaft 51' of the ring 5' to be located on the body of the major shaft 3' so that the center of the ring 5' may align with that of the supporting bite frame 4', thereby being configured at the left or right side of the teeth for x-ray operation; as shown in FIG. 5, when the x-ray operation is performed at a front side of the teeth, the major shaft may be directly employed to connect with the supporting bite frame 4' and the ring 5'; when the x-ray operation is performed for endodontic treatment, because the vertical center of the supporting bite frame 4' is hollow, the reamer 2' is fixedly inserted in the supporting bite frame 4'; correspondingly, in the same manner of connection, the supporting bite frame 4' is reversed to the upper half portion of the teeth so as to perform the x-ray operation at the front, left, and right sides of the upper half portion of the teeth. Although the attachable raying clamp may be used in the teeth diagnosis or the endodontic treatment, the design of the members in combination is more complex; before the members are assembled, the orientation must be determined, so it takes much time in operation and is not suitable for the application due to inconvenience.

SUMMARY OF THE INVENTION

This invention is mainly to provide a dental x-ray clamping device with a multi-orientation support made up with an attachable ring pivot and a supporting-frame pivot, which is designed for an all-purpose modulized raying clamp with simplified members in design, in which the ring pivot is provided with a pivoting ring, while the supporting-frame pivot is provided with a pivoting supporting bite frame, and only the supporting bite frame is pivoted to an opening side of a supporting orientation and combined with the ring pivot easily pivoting at a required angle of elevation so as to be located at an orientation so that the center of the ring aligns with that of the opening side of the supporting bite frame and further that the x-ray operation may be performed at the case of the teeth diagnosis or the endodontic treatment using each orientational support on the teeth, and compared with that of the conventional raying clamp, the determination of the orientation of the support is quite easy and fast.

This invention is further to provide a dental x-ray clamping device with a multi-orientation support, in which the shaft of the ring pivot is additionally provided with an inserted-reamer measuring tank of which the edge may be formed with a scale for the dentist to measure with the inserted reamer in the process of endodontic treatment.

DETAILED DESCRIPTION OF THE INVENTION

Figure 6:
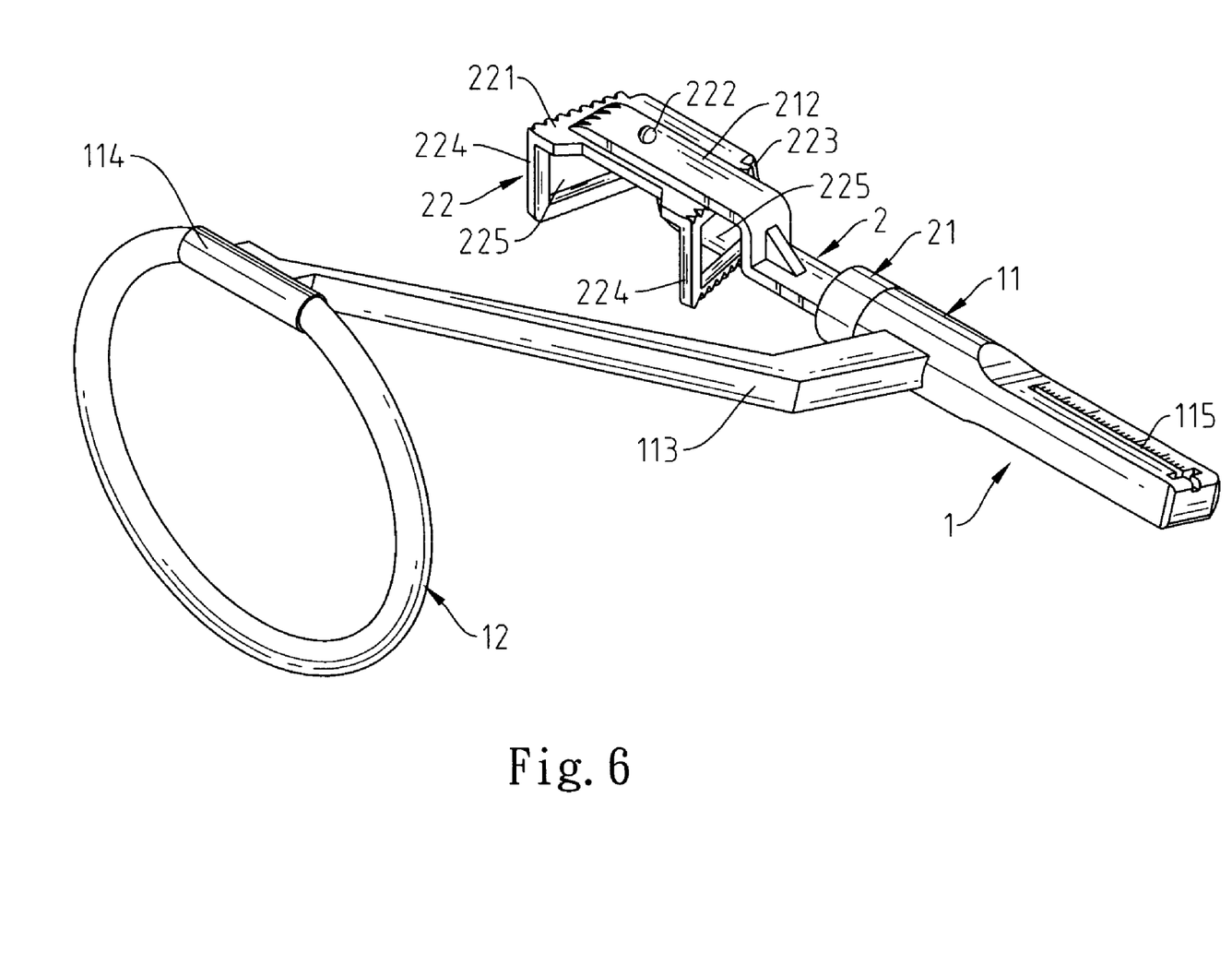
FIG. 6 shows an illustrative outside view according to this invention.
Figure 7:
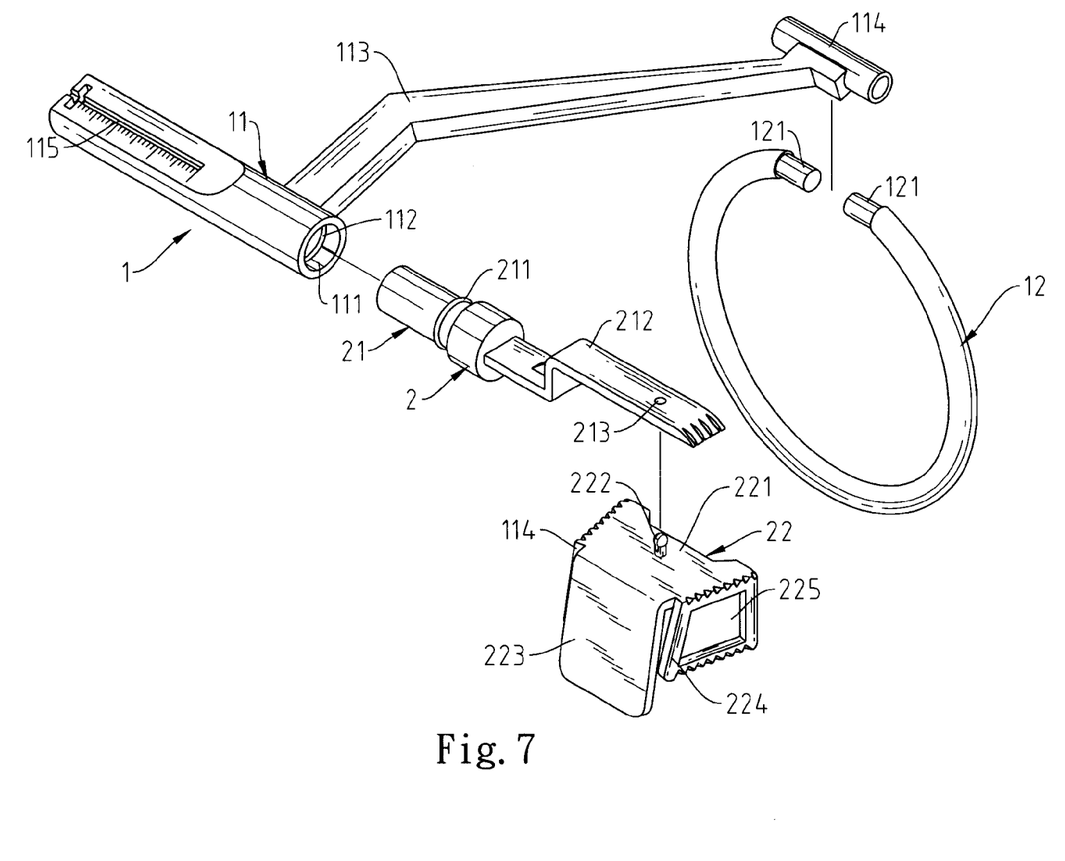
FIG. 7 is a schematic explosion view of the related members according to this invention.

As shown in FIGS. 6 and 7, the dental x-ray clamping device with a multi-orientation support according to this invention mainly comprises a ring pivot 1 and a supporting-frame pivot 2.

The ring pivot 1 is structured with a pivot 11 and a ring 12, in which a pivot hole 111 is formed at a side of said pivot 11 of which the outer margin is formed an all-in-one outward tilt crank 113 and a concaved ring groove 112 is provided near the opening side of the pivot hole 111, in which the end of said crank 113 is formed with a shaft tube 114 parallel with the shaft 11 and the two connection terminals of said ring 12 is separately provided with a connecting pivot 121 to be closely attachable to the shaft tube 114, thereby covering the two sides of the shaft tube 114 to allow the ring 12 to pivot in the shaft tube 114 and then to form an elevation angle of 180 between the ring 12 and the crank 113 for pivoting.

The supporting-frame pivot 2 comprises a pivot 21 and a supporting bite frame 22, in which said pivot is inserted in the pivot hole of the ring pivot 1 to pivot and a flange 211 is provided at the pivot 21 corresponding to the ring groove 112 to wedge the ring groove 112 of the ring pivot 1 so as to prevent the pivot 21 inserted in the pivot hole 111 from falling off and to keep pivoting; further, the front end of said pivot 21 is formed with an all-in-one joint stem 212, in which an insertion hole 213 is provided near the front end of said joint stem 212 so that a supporting bite frame 22, in a shape of U, may be pivoted herein, in which a joint surface 221 of the frame 22 is protruded with a tenon 222 and a clip 223, spaced with a small interval from the two corresponding sides of the frame for an x-ray film to be fixed to, is provided at a side of the joint surface 221 and stretches, and a hollow window 225 is provided between the two corresponding side frame surface of the frame.

Figure 8:
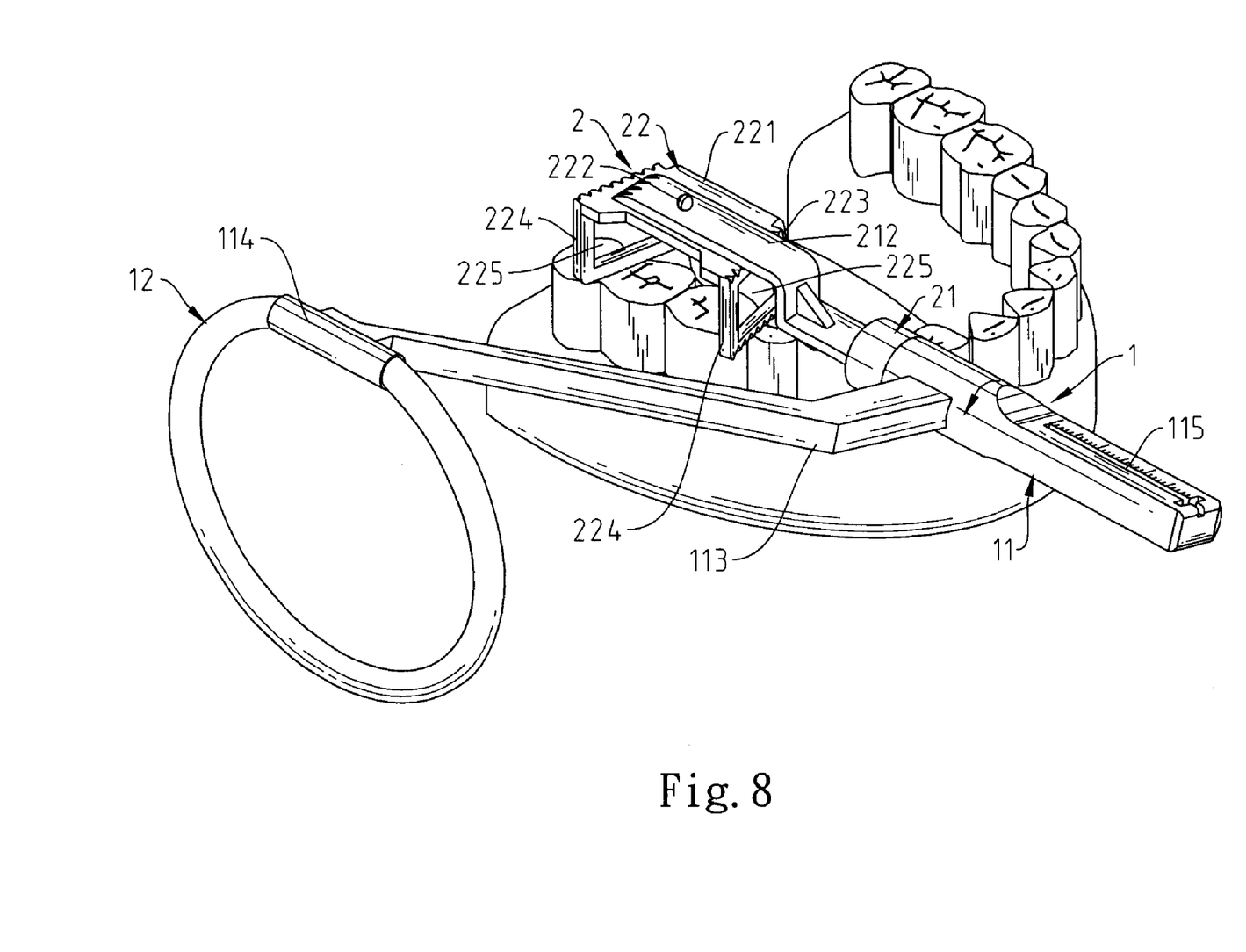
FIG. 8 shows the device supported at the right side of the lower half portion of the teeth for the x-ray operation according to this invention.
Figure 9:
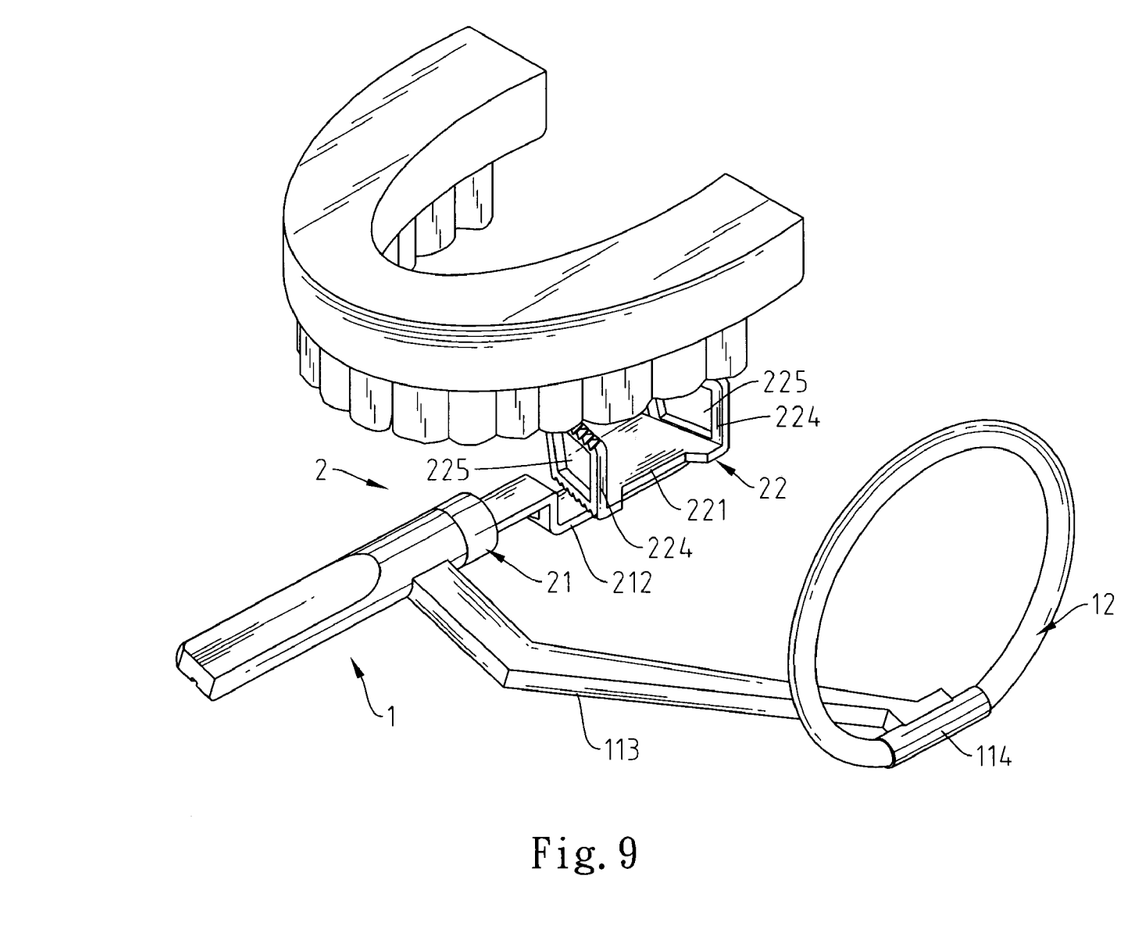
FIG. 9 shows the device supported at the left side of the upper half portion of the teeth for the x-ray operation according to this invention.
Figure 10:
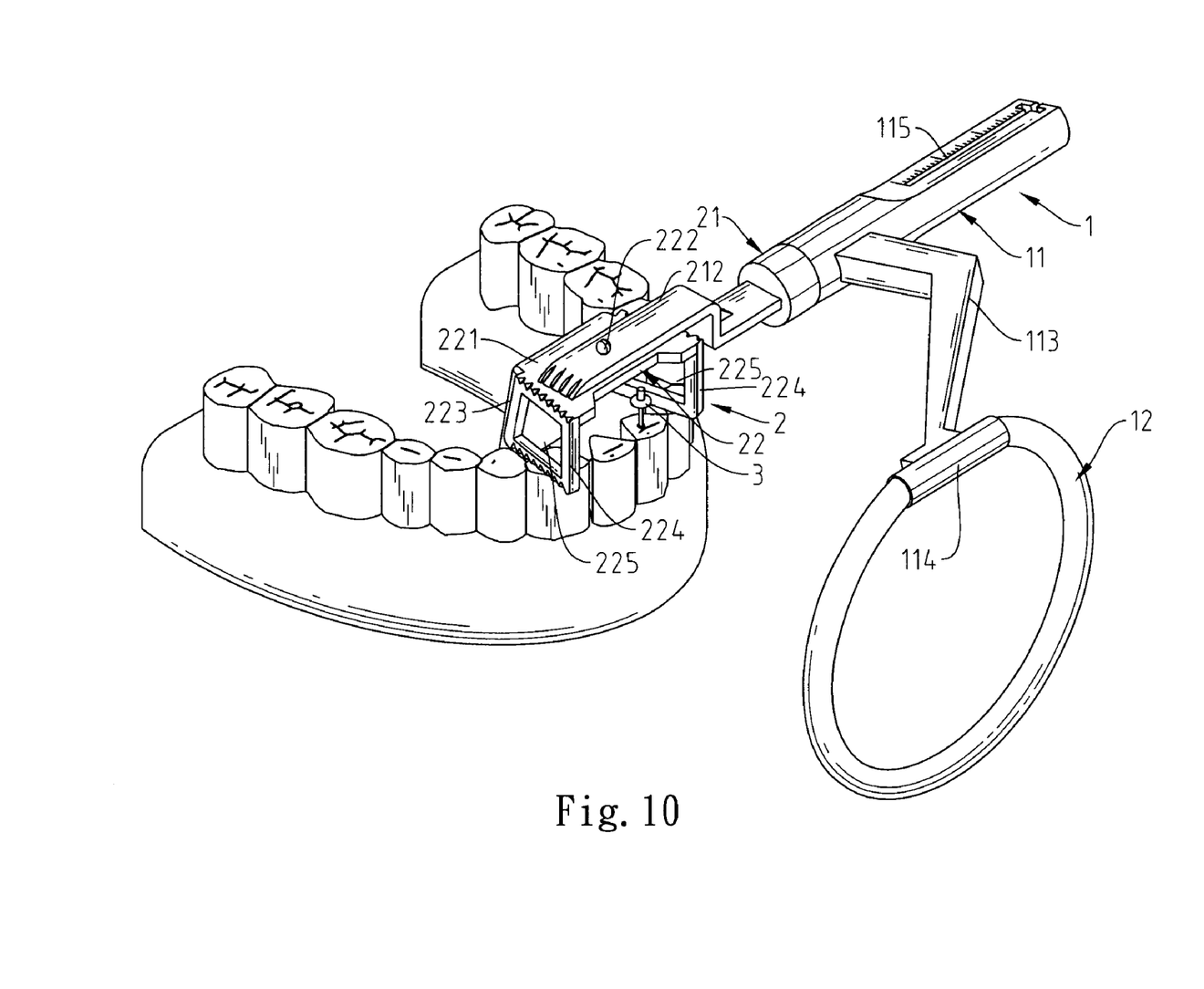
FIG. 10 shows the device supported at the front side of the lower half portion of the teeth for the x-ray operation according to this invention.
Figure 11:
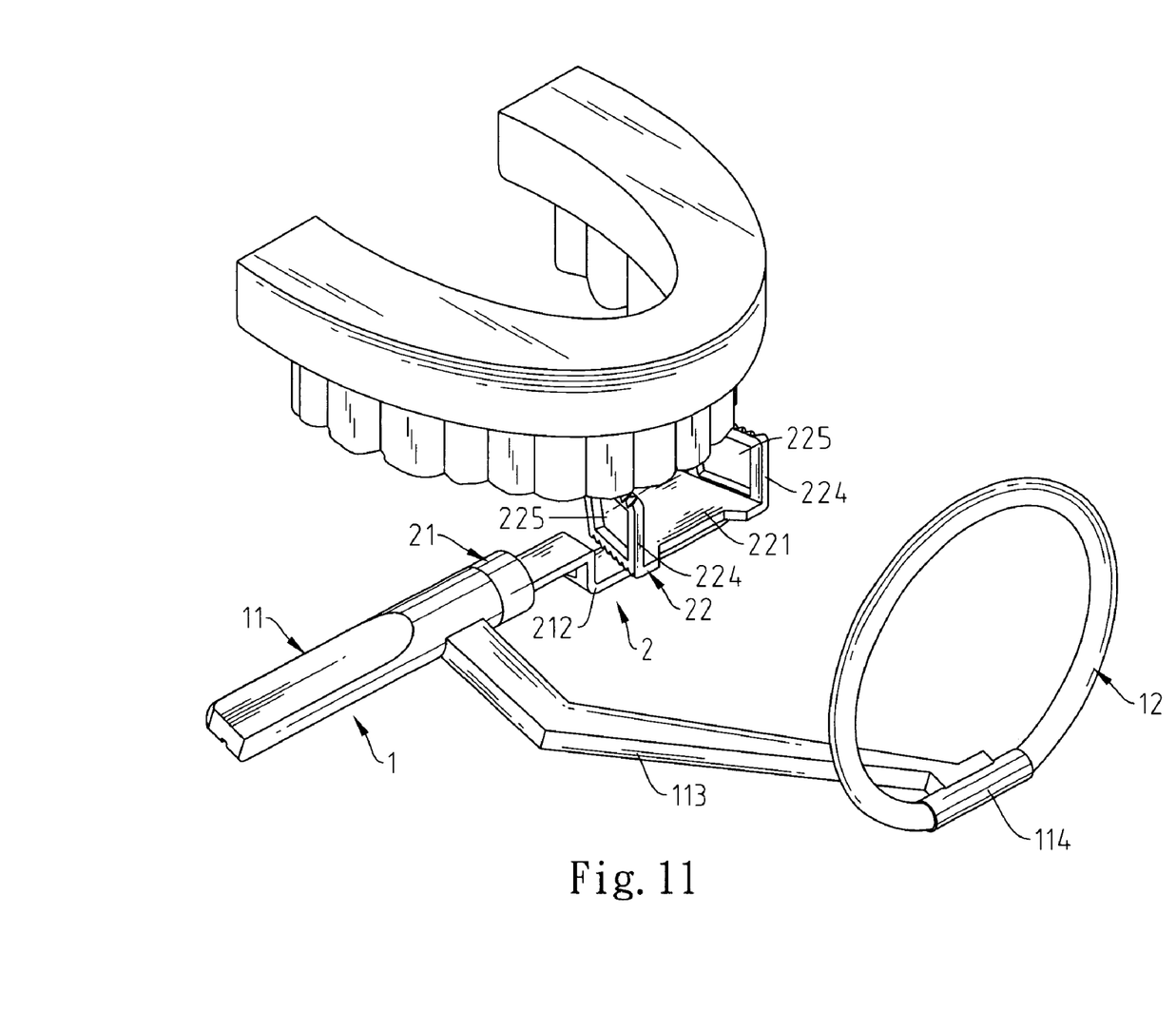
FIG. 11 shows the device supported at the front side of the upper half portion of the teeth for the x-ray operation according to this invention.

When this invention is concretely applied to the x-ray operation at a right inner side of the lower half portion of the teeth, as shown in FIG. 8, the supporting bite frame 22 is allowed to pivot so that the clip 223 which is fixed to the right inner side of the teeth clips the film, and the two corresponding side frame surface 224 of the bite frame 22 is made to place at the top of the teeth so that the outward protruding ring pivot 1 pivots to link with the ring 12 to work and then that the center of the ring 12 aligns with that of the supporting bite frame 22, thereby performing the x-ray operation; next, as shown in FIG. 9, when the x-ray operation is performed at the left side of the upper half portion of the teeth, the raying clamp as shown according to a fixed state in FIG. 8 may be reversed to the changed location so that the supporting bite frame 22 is made to be fixed at the left side of the upper half portion of the teeth, thereby being directly applied to the x-ray operation; also, as shown in FIG. 10, when the x-ray operation is performed at the front side of the lower half portion of the teeth, the raying clamp as shown according to a fixed state in FIG. 8 may be employed to place at the front side of the lower half portion of the teeth without a changed corresponding site between the bite frame 22 and the ring 12; relatively, as shown in FIG. 11, when the x-ray operation is performed at the front side of the upper half portion of the teeth, the raying clamp as shown according to a fixed state in FIG. 10 may be reversed to the changed location so that the supporting bite frame 22 is made to be fixed at the front side of the upper half portion of the teeth, thereby being directly applied to the x-ray operation.

Figure 12:
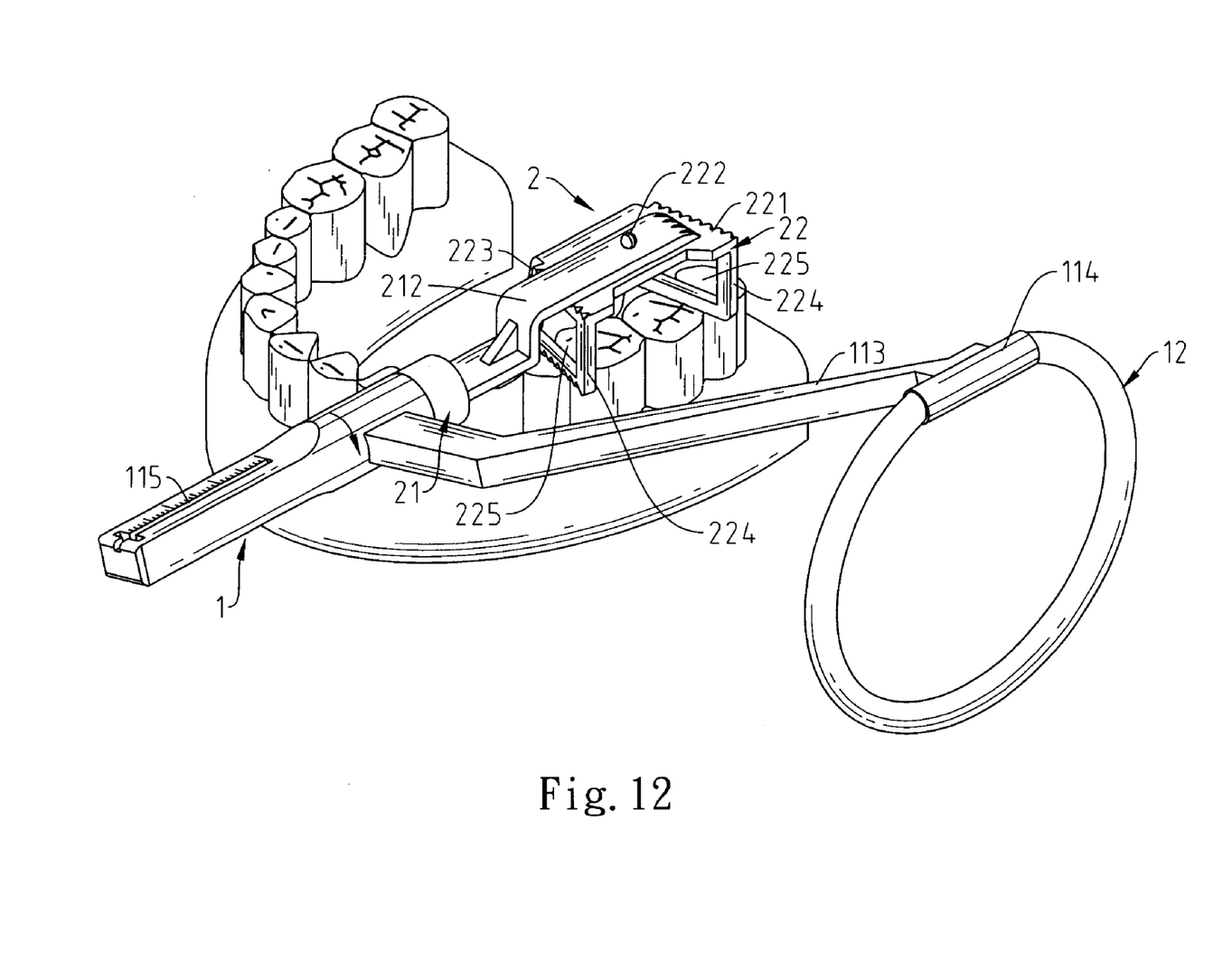
FIG. 12 shows the device supported at the left side of the lower half portion of the teeth for the x-ray operation according to this invention.
Figure 13:
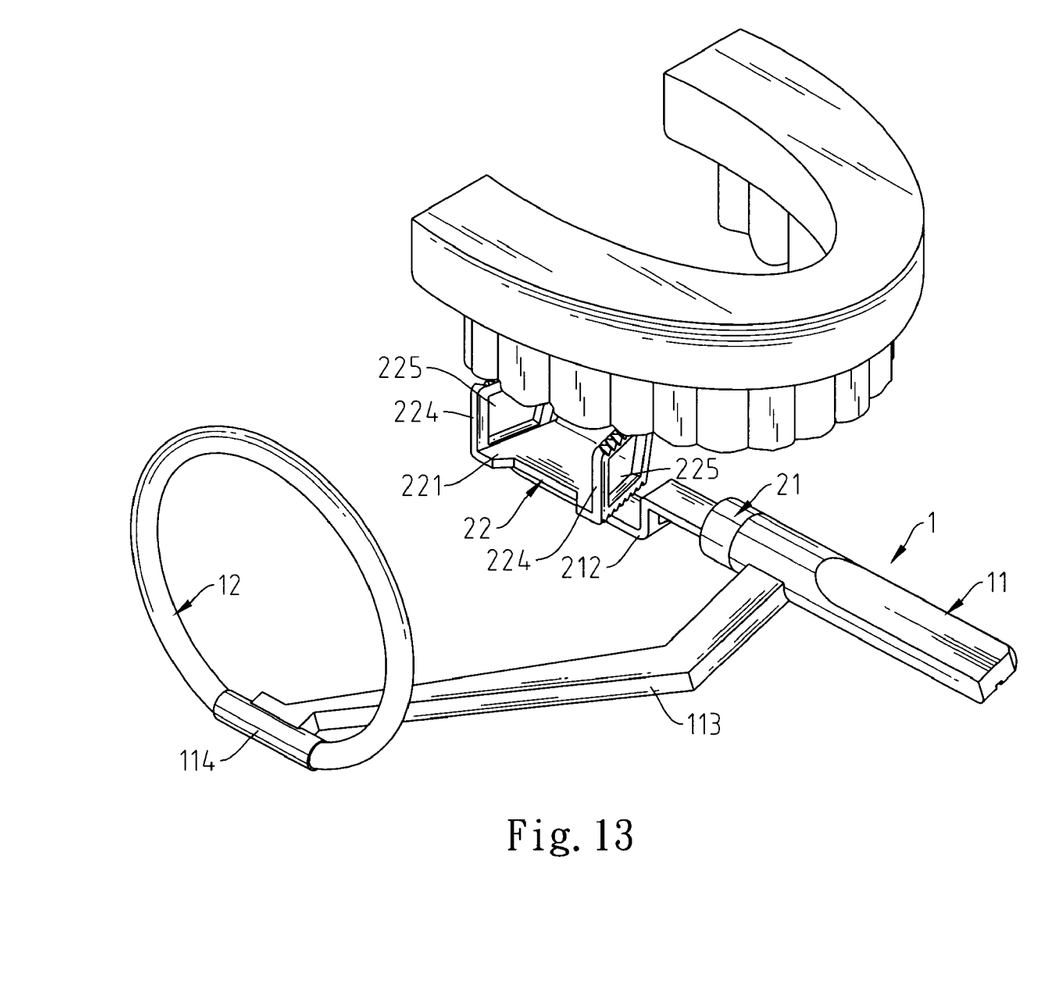
FIG. 13 shows the device supported at the right side of the upper half portion of the teeth for the x-ray operation according to this invention.

Furthermore, as shown in FIG. 12, when the x-ray operation is performed at the left side of the lower half portion of the teeth, the supporting site of the supporting bite frame 22 is reversed at an angle of 180 so that the clip 223 is made to place at the left inner side of the teeth to clip the film and that the two corresponding side frame surface 224 of the bite frame 22 is fixed at the top of the teeth to allow the outward protruding ring pivot 1 to again reversely pivot and then to link with the ring at the right side of the teeth and to next allow the ring 12 to downward pivot, which will make the center of the ring 12 align with that of the bite frame 22, thereby performing the x-ray operation; next, as shown in FIG. 13, when the x-ray operation is performed at the right side of the upper half portion of the teeth, the raying clamp as shown according to a fixed state in FIG. 12 may be reversed to the changed location so that the supporting bite frame 22 is made to be fixed at the right side of the upper half portion of the teeth, thereby being directly applied to the x-ray operation.

From the above-mentioned operation, the x-ray operation may be implemented for the teeth diagnosis using the support at each orientation on the teeth when the supporting bite frame 22 is employed to set a support orientation at the opening side for the pivoting conversion and the ring 12 may easily pivot at an angle of elevation to allow the center of the ring 12 to align with that of the opening side of the supporting bite frame 22.

Also, the raying clamp according to this invention is applied to the endodontic treatment, as shown in FIG. 10, in which the hollow space may be kept at the opening of the supporting bite frame 22 to allow the reamer inserted 3 to be smoothly inserted in the occlusion area of the teeth for the endodontic treatment and then to make the two corresponding side frame surface 224 of the supporting bite frame 22 to be fixed at the top of the teeth, favorably performing the x-ray operation for the endodontic treatment; further, an insertion site of the inserted reamer 3 may be found using the designed hollow window in the middle of the two opposite side frame surface 224 of the supporting bite frame 22.

Figure 14:
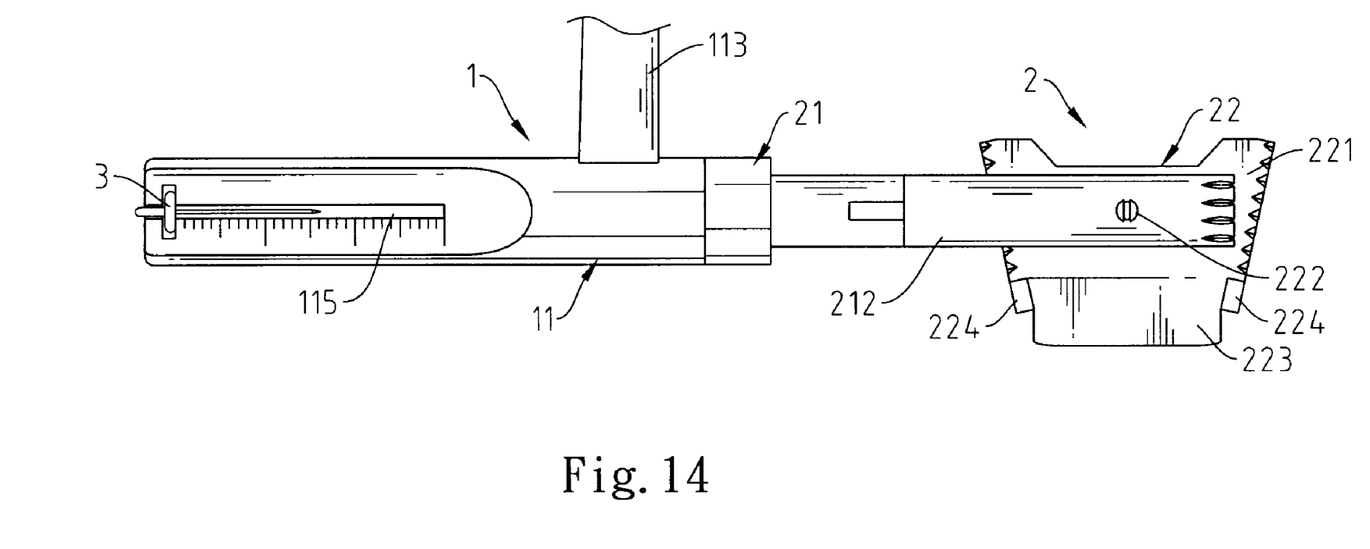
FIG. 14 shows a view of an inserted reamer scale for length measurement according to this invention.

Additionally, conventionally the dentist is required to measure the length of the inserted reamer 3 using an additional gauge at the case of the endodontic treatment, so in order to reduce the cost of a detection module used in the endodontic treatment, the shaft 11 of the ring pivot 1 according to this invention, as shown in FIG. 14, is further provided with an inserted-reamer measuring tank 115 of which the edge may be formed with a scale so that the dentist, inserting a reamer 3 at the case of endodontic treatment, may insert the reamer in the inserted-reamer measuring tank 115 to measure the length using the scale to facilitate the measurement of the inserted reamer 3, thereby replacing the conventional gauge required at the time of reamer insertion so as to lower the cost of the detection module.

The dental x-ray clamping device with the multi-orientation support according to this invention is the designed all-purpose modular raying clamp simply structured with the ring pivot 1 provided with the pivoting ring 12, the supporting-frame pivot 2 provided with the pivoting bite frame 22, in which only the supporting bite frame 22 is pivoted to an opening side of a supporting orientation and combined with the ring pivot 1 to pivot to a changed orientation, and the ring 12 may easily pivot for a changed angle of elevation on the ring pivot 1 to allow the center of the ring 12 to align with that of the opening of the supporting bite frame 22, thereby being further suitable for the x-ray operation at the time of teeth diagnosis or endodontic treatment using the support on the teeth at each orientation, and compared with that of the conventional raying clamp, the determination of the orientation of the support is quite easy and fast for the dental use.

What is claimed is:

1. A dental x-ray clamping device with a multi-orientation support, comprising:

a ring pivot provided with a pivot internally formed with a pivot hole of which an outer margin is made with an all-in-one crank of which a terminal is provided with an all-in-one shaft tube of which two terminals are used for an inserted ring to pivot;

a supporting-frame pivot provided with a pivot inserted in the pivot hole of the ring pivot, of which a front end is made with an all-in-one joint stem of which a surface near the front end is pivoted with a supporting bite frame able to pivot;

in which said supporting bite frame may pivot to change the orientation of the support to an orientation of the teeth and may go with the ring pivot to pivot on the supporting-frame pivot, and the ring may easily pivot on the ring pivot to change for a required angle of elevation so that a center of the ring aligns with that of an opening of the supporting bite frame for the x-ray operation of the device supported at each orientation of the teeth at the time of teeth diagnosis or endodontic treatment.

2. The dental x-ray clamping device with the multi-orientation support as claimed in claim 1, in which two butt terminals of the ring of the ring pivot are separately provided with a connecting pivot closely attachable to the shaft tube, in which the shaft tube is used to have the ring pivot oriented and to form an angle of elevation to the crank.

3. The dental x-ray clamping device with the multi-orientation support as claimed in claim 1, in which the pivot hole in the pivot of said ring pivot is provided with a ring groove near the opening.

4. The dental x-ray clamping device with the multi-orientation support as claimed in claim 1, in which the outer margin of the pivot of said supporting-frame pivot is provided with a flange.

5. The dental x-ray clamping device with the multi-orientation support as claimed in claim 1, in which the joint stem of said supporting-frame pivot is provided with an insertion hole near the stem of the front end.

6. The dental x-ray clamping device with the multi-orientation support as claimed in claim 1, in which the supporting bite frame of said supporting-frame pivot is formed with a tenon.

7. The dental x-ray clamping device with the multi-orientation support as claimed in claim 1, in which the supporting bite frame of said supporting-frame pivot is formed with a hollow window at two opposite side frames.

8. The dental x-ray clamping device with the multi-orientation support as claimed in claim 1, in which the supporting bite frame of said supporting-frame pivot is made with an all-in-one downward clip to space the opposite sides of the supporting-frame pivot so that an x-ray film may be clamped.

9. The dental x-ray clamping device with the multi-orientation support as claimed in claim 1, in which the pivot of the ring pivot is further provided with an inserted-reamer measuring tank of which the edge is formed with a scale.

* * * * *